United States Patent [19]

Tong et al.

[11] 4,441,202

[45] Apr. 3, 1984

[54] SPEECH PROCESSOR

[75] Inventors: Yit C. Tong, Burwood; Peter M. Seligman, Essendon; Graeme M. Clark, Eltham; James F. Patrick, North Melbourne; John B. Millar, Hawker, all of Australia

[73] Assignee: The University of Melbourne, Melbourne, Australia

[21] Appl. No.: 233,585

[22] PCT Filed: May 28, 1980

[86] PCT No.: PCT/AU80/00016
§ 371 Date: Jan. 27, 1981
§ 102(e) Date: Jan. 27, 1981

[87] PCT Pub. No.: WO80/02767
PCT Pub. Date: Dec. 11, 1980

[30] Foreign Application Priority Data

May 28, 1979 [AU] Australia .............................. PD8973
Dec. 19, 1979 [AU] Australia .............................. PE1775

[51] Int. Cl.³ .......................... G10L 1/00; H04R 29/00
[52] U.S. Cl. ..................................................... 381/68
[58] Field of Search ......... 179/1.5 A, 107 R, 107 FD; 381/46, 47, 68, 69

[56] References Cited

U.S. PATENT DOCUMENTS 3,989,904 11/1976 Rohrer et al. .............. 179/107 FD
4,051,331 8/1977 Strong ............................ 179/107 R
4,063,048 12/1977 Kissiah ........................... 179/107 R

FOREIGN PATENT DOCUMENTS 41061 10/1978 Australia .
2811120 9/1978 Fed. Rep. of Germany .
1155422 6/1969 United Kingdom .

OTHER PUBLICATIONS

Mladejousky et al., "A Computer-Based Stimulation ... ", IEEE Trans. on Biomed. Eng., Jul. 1976, pp. 286-295.
Clark et al., "A Multiple-Electrode Hearing Prosthesis ... ", Med. Prog. Tech., vol. 5, pp. 127-140, 1977.

*Primary Examiner*—E. S. Matt Kemeny
*Attorney, Agent, or Firm*—Cushman, Darby & Cushman

[57] ABSTRACT

A system for converting a speech signal into a data signal for controlling an implantable stimulation electrode array hearing prosthesis. An input speech signal is passed through three circuit arms, comprising filter circuits, zero crossing counter circuits and RMS measuring circuits (3-13), for producing signals representing amplitude and frequency of the fundamental voicing component and the first three formants of the speech signal. Computer (14) is programmed with a patient's psychophysical data, and determines the manner of stimulation of the electrodes by ranking the sharpness of the electrodes and assigning sub-bands of the second formant frequency range to particular electrodes. Also, the voiced or unvoiced nature of the signal is determined by comparing the fundamental and second formant components. The output signal passed through a data formatter (15) and transmitter (16) has both formant and prosodic information whereby the production of confusing percepts is avoided.

19 Claims, 5 Drawing Figures

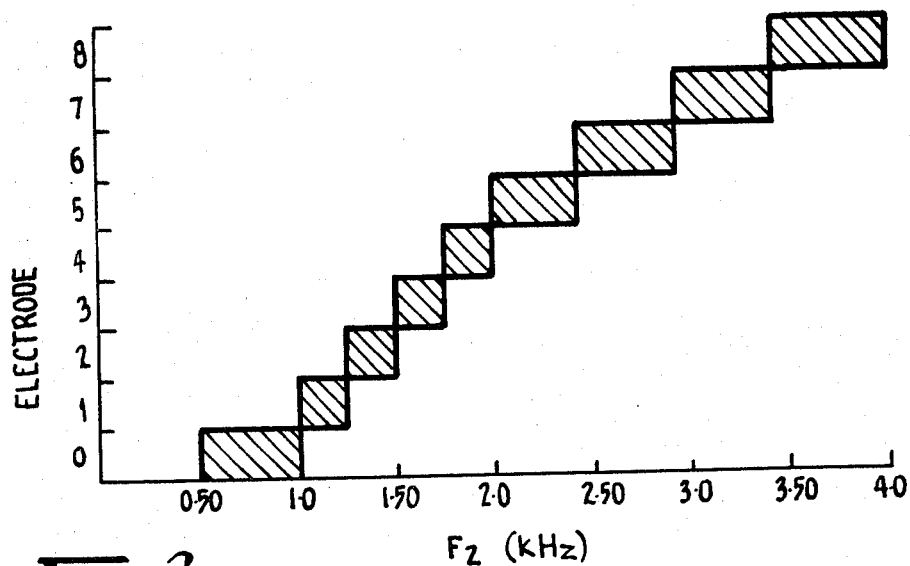
_FIG. 2._
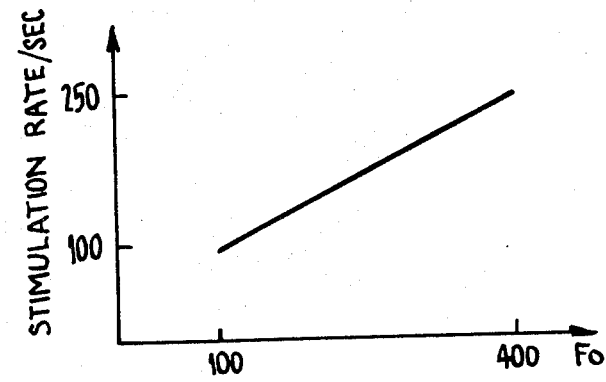
_FIG. 3._
_FIG. 4._
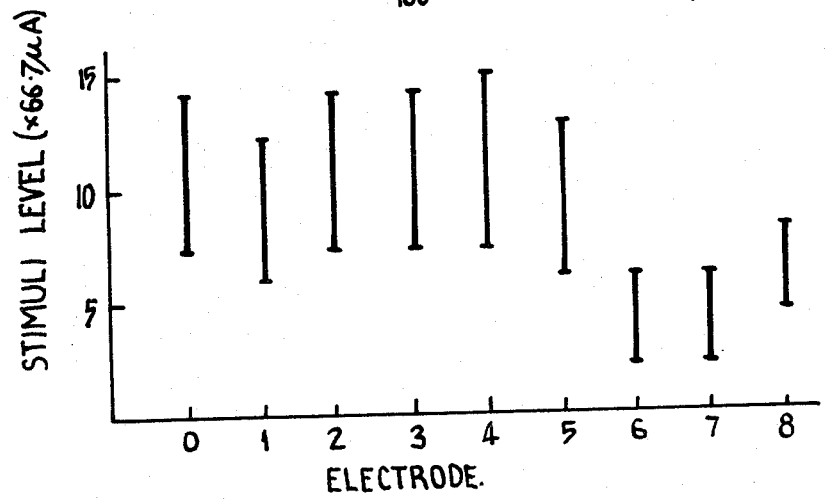

SPEECH PROCESSOR

This invention relates to signal processing systems of the type which are suitable for use with implanted hearing prostheses which electronically stimulate the auditory nerves to produce auditory-like sensations.

In order to best utilize an auditory prostheses for speech communication, a signal processor is required which codes the speech signal into a stimulus pattern. Such signal processors in the past have fallen into two general categories:

1. Those which stimulate electrodes in regions where, according to the place-pitch theory of hearing, they would be stimulated in a normal hearing person. Stimulation occurs at rates corresponding to the frequency of vibration of that portion of the basilar membrane.

2. Those which stimulate at one or more positions in the cochlea but with a stimulus common to all electrodes and at a rate equal or proportional to the glottis pulse rate of the speech signal.

Whilst speech processors which fall into category 1 provide the formant information of the speech signal, they fail to provide prosodic information. Furthermore, since the spectral energy is distributed over broad peaks, confusing percepts may be heard by the patient. Speech processors which fall into category 2 provide the prosodic information important as an aid to lip reading, but fail to provide the necessary formant frequency information.

It is the aim of the present invention to overcome these disadvantages by providing a speech processor having an output signal in which both formant and prosodic information is present whereby the production of confusing percepts is avoided.

The speech processor according to the invention is particularly adapted for use with the implantable hearing prosthesis and the associated stimulation electrode array described in our Australian Patent Applications Nos. AU-A 41061/78 and AU-A 46563/79, respectively.

As described in the earlier Applications referred to above, the hearing prosthesis includes an electrode array which is implanted within the scala tympani region of the cochlea so as to cause stimulation of the auditory nerve fibers by the application of electrical currents of varying levels of intensity and stimulation frequency. Psychophysical tests are used to determine the sharpness ranking of each electrode and a programmable means within the speech processor is programmed to cause stimulation of selected electrodes depending on the characteristics of at least one of the time varying parameters which essentially describe the speech signal within any defined time period.

Experiments have shown that different spectral colours can be cued by the activation of individual electrodes in the array, and for this reason the determination of the sharpness ranking of each electrode in the array is important. The sharpness ranking may be determined in many ways. In the present case, an indirect procedure has been developed to obtain an indication of the variation of spectral colour amongst electrodes. Stimuli in the form of 300 ms pulse trains with rise-decay times of 50 ms and a pulse rate of 100 pps were delivered to single electrodes at current levels determined by balancing the loudness across the electrodes. Each patient is presented with two pulse trains separated in time by a one second interval and is asked to indicate whether the sensation produced by the second stimulus was duller or sharper than the first. In this way, the sharpness ranking of each electrode can be determined relative to the other electrodes for subsequent use in programming the speech processor.

Our experiments have established that the amplitudes and frequencies of the fundamental voicing component and the second formant component of the speech signal may be successfully used to essentially define the speech signal for utilization by the prosthesis to cause stimulation of the auditory nerves within a patient to produce auditory-like sensations. To achieve this end, the estimated second formant frequency is mapped so that selected segments of the range of second formant frequencies usually experienced are associated with individual electrodes in the array. The mapping is preferably arranged so that the higher levels of the second formant frequency are associated with the electrodes having greater sharpness ranking and the electrodes in the array are then selected according to the map for stimulation as the second formant frequency is estimated. Electrode selection is achieved by programming the programmable means for each particular patient in accordance with the second formant frequency/sharpness map referred to above. The level of stimulation of each electrode is determined by the estimated amplitude of the second formant component.

It will be appreciated that in speech, some sounds are unvoiced: they are not produced by a vibration of the glottis, but merely by the movement of air. Thus, in order to produce the necessary perception of realistic auditory-like sensations within the patient, the speech processor must include means to determine whether the speech signal is voiced or unvoiced at any one time. For this reason, the speech processor is provided with means for detecting whether the speech signal is voiced or unvoiced and for causing the programmable means to output data to cause stimulation of the selected electrode at a pulse rate which is related to the estimated frequency of the fundamental voicing component of the speech signal for voiced speech components. Where unvoiced speech components are detected, the selected electrode is stimulated at a lower constant pulse rate which results in a rough sounding percept akin to the unvoiced sound.

Detection of the voiced or unvoiced nature of the speech signal may be achieved by programming the programmable device to compare the instantaneous values of the second formant frequency and the amplitude of the fundamental voicing component. Alternatively, this decision may be made by comparing the low frequency signal energy with the simultaneous high frequency energy.

To allow for possible future developments, the frequencies and amplitudes of the first and third formants of the speech signal may also be estimated although this data is not used in the embodiments of the speech processor to be described in further detail below.

Estimation of the second formant frequency of the speech signal is not straightforward since its frequency range overlaps with that of the first formant (at low F2 values) and that of the third formant (at high F2 values). While a bank of narrow band pass filters may be used to estimate the overall signal spectrum, and from which the F2 value can be determined, this type of processing is too involved. In a preferred form of the invention, a single high pass filter is used to produce an output signal in which the second formant frequency component dominates the first and third formant components whereby the second formant frequency may be estimated directly. In one preferred form to be described below, a two pole filter having a 1500 Hz cutoff point and a Q=2 is used to achieve this effect. Following filtering in this manner, the signal may be passed through a zero crossings counter which estimates the frequency of the second formant component over a short period. The amplitude of the second formant component may be estimated by passing the filtered signal through an RMS measuring circuit which provides an estimate of the amplitude of the second formant component. Alternatively, similar results may be obtained by averaging the signal because the signal after filtering is close to sinusoidal in form.

Referring now to the drawings, preferred embodiments of the speech processor according to the invention will now be described in more detail. In the drawings:

FIG. 2 is a typical map which relates the second formant frequency with the various electrodes in the hearing prosthesis;

FIG. 3 is a graph showing the relationship between the fundamental voicing frequency and the pulse rate at which each electrode in the prosthesis is stimulated for voiced speech segments;

FIG. 4 is a graph showing the range of stimulus amplitudes for each electrode in a typical patient.

Figure 1:
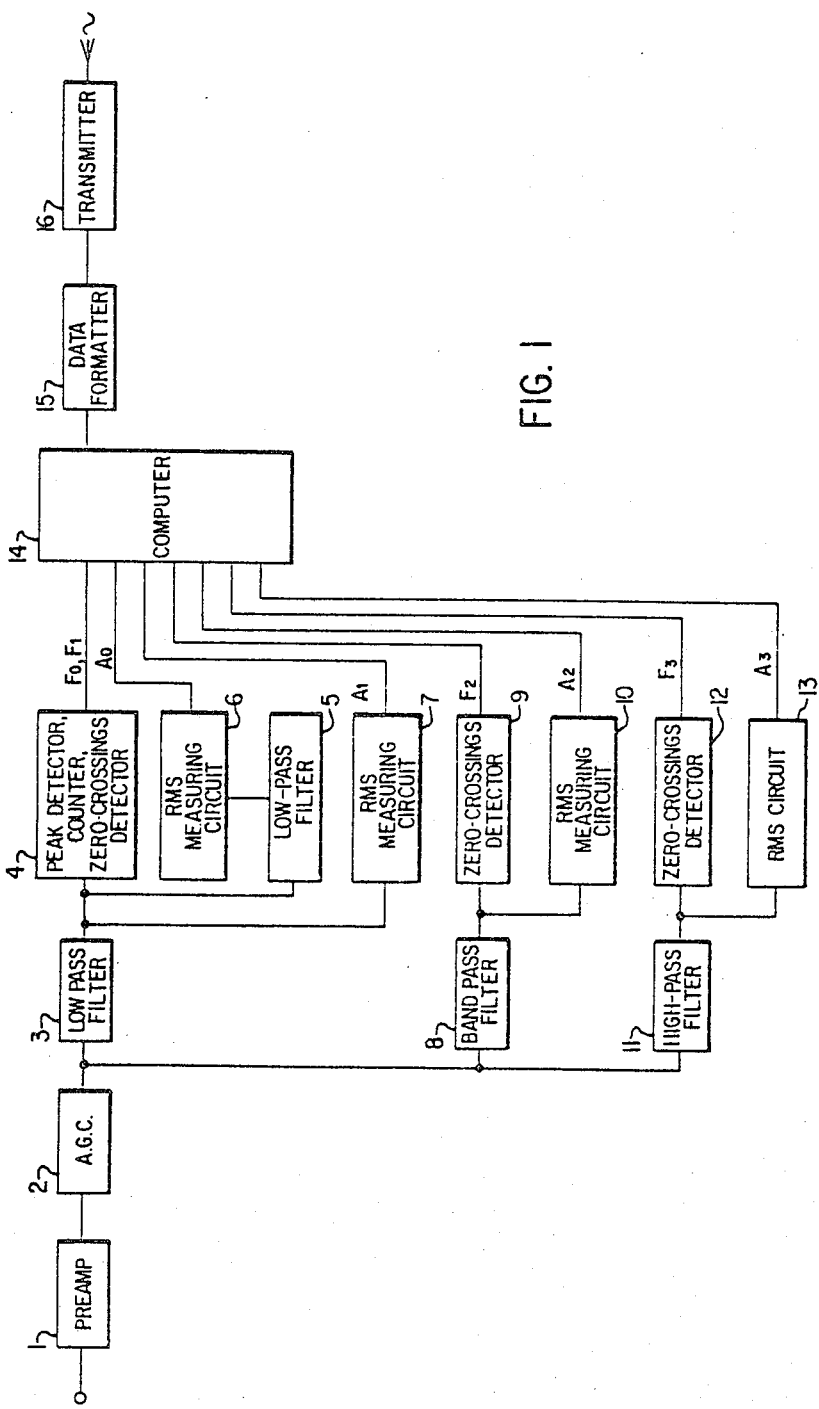
FIG. 1 is a schematic block diagram of a laboratory embodiment of the speech processor system.

Referring now to FIG. 1, the speech processing system comprises a preamplifier 1 which amplifies the analog signal produced by a microphone receiving the speech wave form, and an automatic gain control circuit 2 which keeps the peak signal level nearly constant for a wide range of input signal amplitudes. The signal is passed through three circuit arms for the production of parameter estimates representing the amplitude and frequency of the fundamental voicing component (A0, F0) and the first three formants (A1 F1, A2 F2 and A3 F3) of the speech signal.

The fundamental amplitude and frequency (A0 F0) and the amplitude and frequency of the first formant component (A1, F1) are extracted by passing the signal through a low pass filter 3, preferably a four pole filter having a 1000 Hz cutoff, following which the signal is passed through circuitry 4 which extracts F0 and F1. This circuitry 4 may take the form of a peak detector and counter which estimates F0 combined with a zero crossings detector which enables the time interval between the first two zero crossings following the first peak to be timed to estimate half the period of F1. The fundamental amplitude A0 is estimated by passing the filtered signal through a further low pass filter 5 having a 300 Hz cutoff following which the signal is passed through an RMS measuring circuit 6, such as an AD 536. The amplitude of the first formant A1 is estimated by passing the signal from the first low pass filter 3 through a similar RMS measuring circuit 7.

The amplitude A2 and frequency F2 of the second formant component are estimated by passing the speech signal through a filter 8, which effectively operates as a band pass filter, followed by a zero crossings counter circuit 9 which estimates F2 over a 10 ms Period, and an RMS measuring circuit 10 which estimates A2. As described above, the filter is a two pole high pass filter having a 1500 Hz cutoff and a Q=2. The filter has a skirt characteristic which effectively ensures that undesirable contributions to F2 by the first and third formant components can be ignored by the zero crossings counter and the RMS circuit. In other words, by virtue of the characteristics of the filter, F2 always dominates any contributions by the other two formants.

The amplitude A3 and frequency F3 of the third formant component are similarly estimated using a high pass filter 11 having a 1600 Hz cutoff, a zero crossings counter 12 and an RMS circuit 13.

The above parameter estimates are made available at the input to a computer 14, although as mentioned above only A0, F0 and A2 and F2 are used in the present simple embodiment. It is envisaged that further research will be carried out to determine whether all of the parameters may be used, for example in a weighted spectrum, to achieve better results. However, at the present time, the use of the fundamental and second formant parameters would seem to be capable of producing acceptable results.

The computer 14 is programmed with psychophysical data relating to a particular patient and which determines the manner of stimulation of the implanted electrodes. FIG. 2 shows a typical map relating the electrode number with the frequency F2. The electrodes are ranked for sharpness and the F2 frequency range divided into sub bands with each sub band assigned to a particular electrode. The sub band of lowest frequency is assigned to the electrode with the dullest sensation while the sub band of highest frequency is assigned to the electrode with the sharpest sensation. Although the map of FIG. 2 shows the relationship between F2 and electrode number as being substantially linear, this is not essential and depends on the psychophysical tests carried out on each patient. In preparing the map, account must be taken of the errors in the estimated amplitude A2 of the second formant component introduced by the use of the filter 8.

FIG. 4 of the drawings is a graph which shows the sensitivity of each electrode of a prosthesis implanted within a typical patient. The lower curve of the graph represents the minimum stimulation current that may be applied to each electrode so as to be detectable by the patient while the upper curve sets the maximum level of stimulation current that may be applied without causing discomfort to the patient. The computer 14 is programmed with this information and each selected electrode is caused to be stimulated at a current level lying within the range defined by FIG. 4 and depending on the amplitude A2 of the second formant component such that stimulation current levels nearer to the upper curve are applied for high levels of A2 and nearer to the lower curve for low levels of A2.

The computer 14 is also programmed to control the rate at which the various electrodes are stimulated in a manner which is proportional to the estimated fundamental voicing frequency F0. FIG. 3 shows a typical relationship between F0 and stimulation rate, although once again the relationship may be varied.

For unvoiced speech components, the computer is programmed to apply a constant stimulation rate of fifty stimulations per second. The computer is programmed to detect a voiced speech segment when F2 is low and A0 is high and an unvoiced speech segment when F2 is high and A0 is low.

The data output from the computer is passed through a data formatter 15 which converts the data into a form which is suitable for transmission by the transmitter 16 to the implanted prosthesis. The data signal received by the implanted prosthesis is then converted in the manner described in Application No. 41061/78 into stimulation currents which are applied to the required electrodes at the level of intensity and stimulation rate dictated by the computer on the basis of the information programmed therein and the parameter estimates received from the parameter estimating currents described above.

Figure 5:
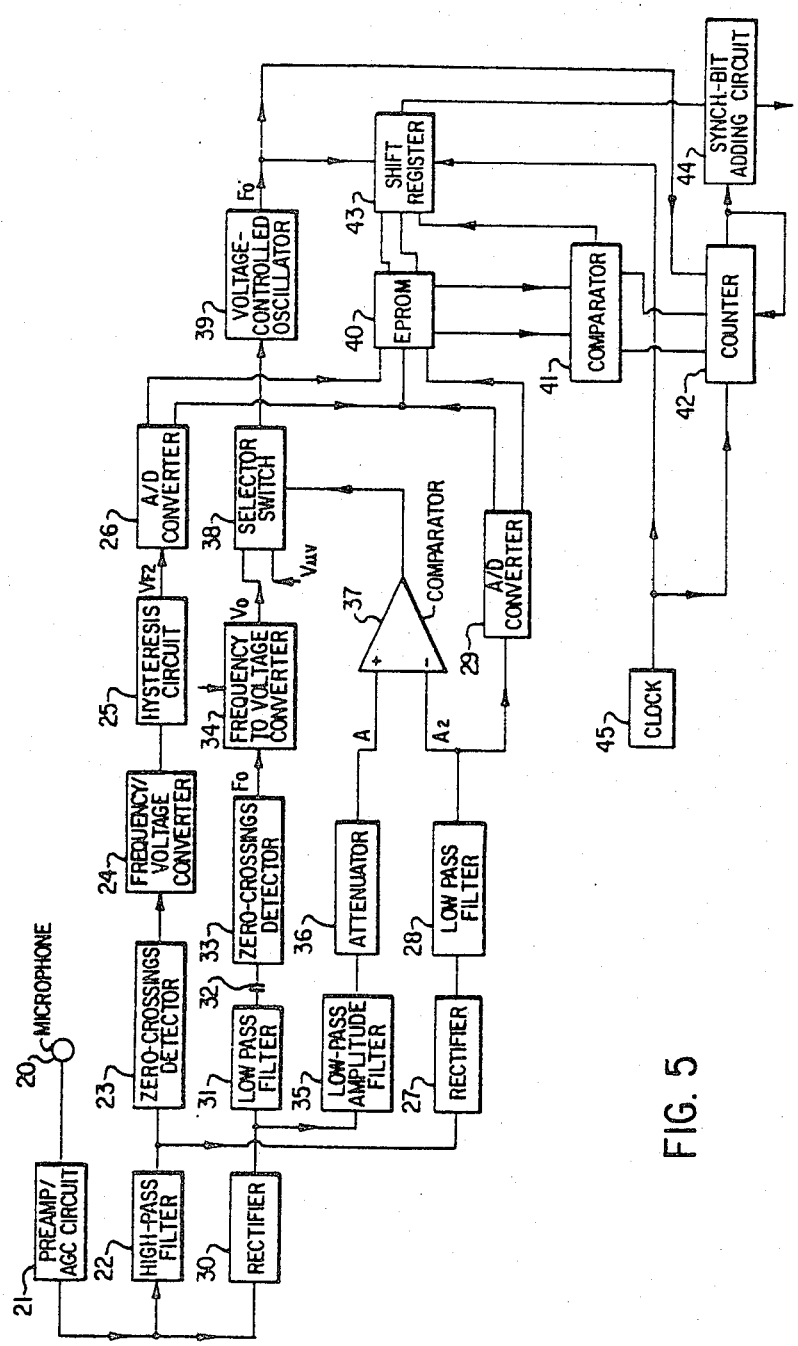
FIG. 5 is a schematic block diagram of a simple hard-wired speech processor system embodying the invention.

Referring now to FIG. 5 of the drawings, the simple hardwired speech processor shown in block diagram form is designed to implement with a minimum hardware and power consumption a speech processing strategy based on the presentation of the amplitude and frequency of the second formant only of the speech signal, which is represented by stimulation of one electrode at a time at a rate proportional to the frequency of the fundamental voicing component (glottal pulse frequency F0).

The system shown once again includes a microphone 20 for receiving the speech signal and a preamplifier/automatic gain control circuit 21 which maintains the output peak signal level nearly constant over a wide range of input signal amplitudes. The second formant frequency F2 is estimated from the output of the circuit 21 by means of a high pass filter 22, having the same characteristics as filter 8 of the first embodiment, a zero crossings detector 23, a frequency to voltage converter 24 and a hysteresis circuit 25 which produces a voltage VF2 proportional to F2, following which the voltage is converted to a six bit digital form by an analogue to digital converter 26. The amplitude A2 of the second formant is extracted from the output of the filter 22 by means of a rectifier 27 and a 35 Hz low pass filter 28. The resulting signal is converted to a five bit digital signal by an analogue to digital converter 29.

The frequency F0 of the fundamental voicing component of the speech signal is extracted from the circuit 21 by a rectifier 30, and a 270 Hz low pass filter 31 which together constitute an envelope detector. The undulations of the envelope are separated from the DC level by a capacitor 32, and the zero crossings of the envelope are detected by circuit 33, following which the frequency of the zero crossings is converted to a voltage V0 by a frequency to voltage converter 34.

To establish whether the speech signal is voiced or unvoiced, the amplitude of the signal from rectifier 30 is measured by a 35 Hz low pass amplitude filter 36 following which it is passed via an attenuator 36 to one input of a comparator 37. As described above, a sound is characteristically unvoiced if its high frequency energy is high compared to its low frequency energy. Thus, by adjusting the attenuator 36, the comparator 37 can be made to produce a high output for a voiced signal and a low output for an unvoiced signal.

When the output of the comparator 37 goes high, it actuates a selector switch 38 to pass the voltage V0 from the glottal pulse rate extraction path, and when the output of the comparator 37 goes low, a constant low voltage Vuv is passed to cause stimulation of the implanted electrodes at a low pulse rate, thus producing in the patient a sensation akin to sibilance.

A voltage controlled oscillator 39 converts the output from the selector switch 38 to a frequency corresponding to the rate of stimulation F0'.

The digital amplitude and frequency data corresponding to the amplitude and frequency of the second formant components (A2, F2) are fed to a 16k programmable and erasable read only memory (EPROM) 40. This device accepts the eleven bit input and provides two four bit words corresponding to an electrode number and its level of stimulation. The information included in FIGS. 2, 3 and 4 as described above is programmed into the EPROM 40 so that the two four bit words designate the selected electrode and the desired level of stimulation of that electrode.

The final operation performed by the processor is to code the information into serial data for transmission to the implanted prosthesis. To do this, it is necessary to transmit a synchronization followed by blank seven bit words until the word appropriate to the electrode to be stimulated is reached and then further blank words until 16 words have been transmitted. A second synchronization bit is outputted to initiate stimulation by the implanted prosthesis.

A four bit digital comparator 41 is used to compare the desired electrode number with the output of a mod-16 counter 42. The counter 42 is reset and starts when a scaled "glottal pulse" F0' is received. The counter 42 counts groups of seven clock pulses from the clock circuit 45 until the right word is reached. A parallel load shift register 43 is loaded at the start with the stimulus level and is then enabled and serially outputs its data. The data stream has a synchronization bit added by circuit 44 and holds the output of the reset mode until the next scaled "glottal pulse" is received. The clock and serial data signals pass on to amplifiers and modulators for transmission to the implanted prosthesis via the power and data coil units described in further detail in the co-pending Application referred to above.

It will be appreciated that the above described hardwired embodiment of the invention operates in essentially the same manner as the laboratory embodiment first described above and accordingly further description of its operation is not required for an adequate understanding by a person skilled in the art. The above described embodiments of the invention have been clinically tested with some success. However, the speech processors described are able only to stimulate a single electrode at any one time and further research will be required to determine the manner in which simultaneous multiple electrode stimulation may be implemented and whether multiple electrode stimulation will improve the auditory-like sensations produced in the patient. Similarly, the characteristics of the filter for extracting the second formant frequency have yet to be determined for Australian and other accents. The described system is based on characteristics determined from a U.S. vowel table which may not be correct for Australian conditions.

What we claim is:

1. A signal processing system for converting a speech signal into a data signal for controlling a hearing prosthesis including an implanted electrode array adapted to stimulate the auditory nerve fibres of a patient by the application of electrical currents to selected electrodes in said array, said processing system comprising means (1,2;20,21) for generating an input signal corresponding to a received speech signal, means (3–6;30–36) for estimating the amplitude and frequency of the fundamental voicing component of said speech signal, means (8–10; 22–26, 27, 28) for estimating the amplitude and frequency of the second formant component of said speech signal, means (14;37) for determining whether said speech signal is voiced or unvoiced, programmable means (14;40) for producing instruction data which in use causes the application of said electrical currents to selected electrodes in said array, said programmable means being programmed with data (FIG. 2) defining a predetermined relationship between each electrode and a selected range of said second formant frequencies based on psychophysical testing of the patient and causing selection of said electrodes based on the estimated frequency of said second formant component such as to produce the desired percepts in the auditory-like sensations generated in the patient, means (14;38) for causing stimulation of said selected electrode at a frequency dependent on the estimated frequency of said fundamental voicing component for voiced speech signals and at a lower substantially constant frequency for unvoiced speech signals, said programmable means (14;40) further being programmed to produce data (FIG. 4) which determines the level of stimulation of each selected electrode dependent on said estimated amplitude of said second formant component of said speech signal as well as on predetermined data relating to the sensitivity of each electrode implanted in the patient.

2. The system of claim 1, wherein said programmable means (14;40) is further programmed with data (FIG. 3) defining a pre-determined relationship between the estimated frequency of said fundamental voicing component of said speech signal and the rate at which each said selected electrode is stimulated.

3. The system of claim 2, wherein said stimulation rate has a lower limit and an upper limit, said lower limit being substantially higher than said substantially constant lower frequency and said upper limit being lower than the upper limit of said estimated frequency of said fundamental voicing component.

4. The system of claim 2 or 3, wherein said programmable means (14;40) is further programmed with alternative data defining a different relationship between said electrode stimulation rate and said estimated frequency of said fundamental voicing component which is more suitable for auditory-like sensations resembling music or certain types of speech signal.

5. The system of claim 1, 2 or 3, wherein said programmable means (14;40) is programmed to compare the instantaneous values of the estimated frequency F2 of the second formant component of said speech signal and the estimated amplitude A0 of the fundamental voicing component of said speech signal to determine a voiced speech signal when the instantaneous value of F2 is low and the instantaneous value of A0 is high and to determine an unvoiced speech signal when the instantaneous value of F2 is high and the instantaneous value of A0 is low.

6. The system of claim 1, 2 or 3, wherein means (14,37) are provided to compare the instantaneous high frequency energy of said speech signal with the instantaneous low frequency energy of said speech signal and for causing said selector electrode to be stimulated at said lower substantially constant when said instantaneous high frequency energy is high compared to said instantaneous low frequency energy.

7. The system of claim 1, 2 or 3, wherein the frequency of said second formant component of said speech signal is estimated by means of a single high pass filter (8;22) having characteristics which produce an output signal in which the second formant frequency component of said speech signal dominates the first and third formant frequency components of said speech signal.

8. The system of claim 7, wherein high pass filter (8;22) is a two pole filter having a cutoff point of about of 1500 Hz and a Q of 2, said filter being used in conjunction with a zero crossings counter (9;23) which estimates the said frequency of second formant component over a short period.

9. The system of claim 8, further including a circuit (25) for converting said estimated frequency to a proportional voltage signal and an analogue to digital converter for converting said voltage signal into digital data form.

10. A method of converting a speech signal into a data signal for controlling a hearing prosthesis including an implanted electrode array adapted to stimulate the auditory nerve fibres of a patient by the application of electrical currents to selected electrodes in said array, said method comprising the steps of generating an input signal corresponding to a received speech signal, estimating the amplitude and frequency of the fundamental voicing component of said speech signal, estimating the amplitude and frequency of the second formant component of said speech signal, determining whether said speech signal is voiced or unvoiced, conducting psychophysical testing of a patient to determine a relationship between each electrode and a selected range of said second formant frequencies, selecting at least one of said electrodes on the basis of said estimated second formant frequency and said determined relationship to produce the desired percepts in the auditory-like sensations generated in the patient, causing stimulation of said selected electrode at a frequency dependent on the estimated frequency of said fundamental voicing component for voiced speech signals and at a lower substantially constant frequency for unvoiced speech signals, and causing stimulation of each selected electrode in a manner dependent on the estimated amplitude of said second formant component of said speech signal as well as on predetermined data relating to the sensitivity of each electrode implanted in the patient.

11. A signal processing system for converting a speech signal into a data signal for controlling a hearing prosthesis including an implanted electrode array adapted to stimulate the auditory nerve fibres of a patient by the application of electrical currents to selected electrodes in said array, said processing system comprising:

means (1,2;20,21) for generating an input signal corresponding to a received speech signal, means (3-6;30-36) for estimating the amplitude and frequency of the fundamental voicing component of said speech signal, means (8-10; 22-26, 27, 28) for estimating the amplitude and frequency of at least one formant component of said speech signal, means (14;37) for determining whether said speech signal is voiced or unvoiced, programmable means (14;40) for producing instruction data which in use causes the application of said electrical currents to selected electrodes in said array, said programmable means being programmed with data (FIG. 2) defining a predetermined relationship between each electrode and a selected range of said at least one formant frequencies based on psychophysical testing of hearing impaired persons and causing selection of said electrodes based on the estimated frequency of said at least one formant component such as to produce the desired percepts in the auditory-like sensations generated in the patient, and means (14;38) for causing stimulation of at least one selected electrode at a frequency dependent on the estimated frequency of said fundamental voicing component for voiced speech signals and at a lower substantially constant frequency for unvoiced speech signals, said programmable means (14;40) further being programmed to produce data (FIG. 4) which determines the level of stimulation of each selected electrode dependent on said estimated amplitude of said at least one formant component speech signal as well as on predetermined data relating to the sensitivity of each electrode implanted in the patient.

12. The system of claim 11, wherein said programmable means (14;40) is further programmed with data (FIG. 3) defining a predetermined relationship between the estimated frequency of said fundamental voicing component of said speech signal and the rate at which each said selected electrode is stimulated.

13. The system of claim 12, wherein said stimulation rate has a lower limit and an upper limit, said lower limit being substantially higher than said substantially constant lower frequency and said upper limit being lower than the upper limit of said estimated frequency of said fundamental voicing component.

14. The system of claim 12 or 13, wherein said programmable means (14;40) is further programmed with alternative data defining a different relationship between said electrode stimulation rate and said estimated frequency of said fundamental voicing component which is more suitable for auditory-like sensations resembling music or certain types of speech signals.

15. The system of claim 11, 12 or 13, wherein said programmable means (14;40) is programmed to compare the instantaneous values of the estimated frequency F2 of the second formant component of said speech signal and the estimated amplitude A0 of the fundamental voicing component of said speech signal to determine a voiced speech signal when the instantaneous value of F2 is low and the instantaneous value of A0 is high and to determine the unvoiced speech signal when the instantaneous value of F2 is high and the instantaneous value of A0 is low.

16. The system of claim 11, 12 or 13, wherein means (14,37) are provided to compare the instantaneous high frequency energy of said speech signal with the instantaneous low frequency energy of said speech signal and for causing said selector electrode to be stimulated at said substantially lower constant when said instantaneous high frequency energy is high compared to said instantaneous low frequency energy.

17. The system of claim 15, wherein the frequency of said second formant component of said speech signal is estimated by means of a single high pass filter (8;22) having characteristics which produce an output signal in which the second formant frequency component of said speech signal dominates the first and third formant frequency components of said speech signal.

18. A method of converting a speech signal into a data signal for controlling a hearing prosthesis including an implanted electrode array adapted to stimulate the auditory nerve fibres of a patient by the application of electrical currents to selected electrodes in said array, said method comprising the steps of generating an input signal corresponding to a received speech signal, estimating the amplitude and frequency of the fundamental voicing command of said speech signal, estimating the amplitude and frequency of the at least one formant component of said speech signal, determining whether said speech signal is voiced or unvoiced, conducting psychophysical testing of hearing impaired persons to determine a relationship between each electrode and a selected range of said at least one formant frequencies, selecting at least one of said electrodes on the basis of said estimated at least one formant frequency and said determined relationship to produce the desired percepts in the auditory-like sensations generated in the patient, causing stimulation of said at least one selected electrode at a frequency dependent on the estimated frequency of said fundamental voicing component for voiced speech signals and at a lower substantially constant frequency for unvoiced speech signals, and causing stimulation of each selected electrode in a manner dependent on the estimated amplitude of said at least one formant component of said speech signal as well as on predetermined data relating to the sensitivity of each electrode implanted in the patient.

19. A signal processing system for converting a speech signal into a data signal for controlling a hearing prosthesis including an implanted electrode array adapted to stimulate the auditory nerve fibres of a patient by the application of electrical currents to selected electrodes in said array, said processing system comprising:

means (1,2;20,21) for generating an input signal corresponding to a received speech signal, means (3–6;30–36) for estimating the amplitude and frequency of the fundamental voicing component of said speech signal, means (8–10; 22–26, 27, 28) for estimating the amplitude and frequency of at least one formant component of said speech signal, means (14;37) for determining whether said speech signal is voiced or unvoiced, programmable means (14;40) for producing instruction data which in use causes the application of said electrical currents to selected electrodes in said array, said programmable means being programmed with data (FIG. 2) defining a predetermined relationship between each electrode and a selected range of said at least one formant frequencies based on psychophysical testing of hearing impaired persons and causing selection of said electrodes based on the estimated frequency of said at least one formant component such as to produce the desired percepts in the auditory-like sensations generated in the patient, and means (14;38) for causing stimulation of at least one selected electrode at a frequency dependent on the estimated frequency of said fundamental voicing component for voiced speech signals and at a lower substantially constant frequency for unvoiced speech signals, said programmable means (14;40) further being programmed to produce data (FIG. 4) which determines the level of stimulation of each selected electrode dependent on said estimated amplitude of said at least one formant component and said estimated amplitude of said fundamental voicing component of said speech signal as well as on predetermined data relating to the sensitivity of each electrode implanted in the patient.

* * * * *